United States Patent
Wang et al.

(10) Patent No.: US 9,804,081 B2
(45) Date of Patent: Oct. 31, 2017

(54) DEVICE AND A METHOD OF SENSING CHARACTERISTICS OF A FOOD MATERIAL AND A MACHINE AND A METHOD OF BREWING COFFEE HAVING A WAVE SOURCE WITH WAVELENGTH RANGE COMPRISING VISIBLE BAND AND NEAR INFRARED BAND

(71) Applicant: KONINKLIJKE PHILIPS N.V., Eindhoven (NL)

(72) Inventors: Xiaoxin Wang, Eindhoven (NL); Bin Yin, Eindhoven (NL); Weizhong Chen, Eindhoven (NL); Declan Patrick Kelly, Eindhoven (NL); Wei Li, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 150 days.

(21) Appl. No.: 14/891,798

(22) PCT Filed: May 22, 2014

(86) PCT No.: PCT/IB2014/061612
§ 371 (c)(1),
(2) Date: Nov. 17, 2015

(87) PCT Pub. No.: WO2014/191873
PCT Pub. Date: Dec. 4, 2014

(65) Prior Publication Data
US 2016/0097711 A1    Apr. 7, 2016

(30) Foreign Application Priority Data

May 27, 2013  (WO) ................ PCT/CN2013/076258

(51) Int. Cl.
*G01N 21/27* (2006.01)
*G01N 21/359* (2014.01)
(Continued)

(52) U.S. Cl.
CPC ........... *G01N 21/27* (2013.01); *A23N 12/125* (2013.01); *G01J 1/42* (2013.01); *G01N 21/359* (2013.01);
(Continued)

(58) Field of Classification Search
CPC ...... G01N 21/27; G01N 21/359; A23N 12/10; A23N 12/12
(Continued)

(56) References Cited

U.S. PATENT DOCUMENTS 5,062,066 A * 10/1991 Scher ...................... A47J 27/62
                                                              700/29
6,104,494 A    8/2000 Torbet
(Continued)

FOREIGN PATENT DOCUMENTS

DE       3720388 A1    12/1988
EP       0365205 A2     4/1990
IN    2012MU00404      2/2012

OTHER PUBLICATIONS

A. Voilley & D. Simatos, "Modeling the Solubilization Process During Coffee Brewing", J. of Food Process Eng. 1979, 2, 185.
(Continued)

*Primary Examiner* — Que T Le

(57) ABSTRACT

A device and a method of sensing characteristics of a food material and a machine and a method of brewing coffee. The device comprises: a wave source (20) configured for emitting waves to said food material (22), with the wavelength range of said waves comprising a selected near infrared band neighboring a visible band; a detector (26), configured for
(Continued)

detecting intensities of the waves reflected by said food material; and an analysis module (28), configured for determining said characteristics according to the detected intensity of the reflected waves. Preferably, the food material comprises coffee powder, and the characteristics comprise at least any one of: color of the coffee powder (corresponding to the roasting degree of coffee powder); and grind fineness of the coffee powder.

12 Claims, 3 Drawing Sheets

(51) Int. Cl.
*A23N 12/12* (2006.01)
*G01J 1/42* (2006.01)
(52) U.S. Cl.
CPC . *G01N 2201/061* (2013.01); *G01N 2201/068* (2013.01)

(58) Field of Classification Search
USPC .................................. 250/221, 559.4, 214.1
See application file for complete search history.

(56) References Cited

U.S. PATENT DOCUMENTS

| 6,106,877 | A | 8/2000 | Allington |
| 7,285,300 | B1 | 10/2007 | Allington |
| 2001/0055116 | A1 | 12/2001 | Maczura |
| 2007/0211247 | A1 | 9/2007 | Tsenkova |

OTHER PUBLICATIONS

S. Andueza, M. Paz De Pen, C. Cid, Chemical and Sensorial Characteristics of Espresso Coffee as Affected by Grinding and Torrefacto Roast, J of Food Chem. 2003, 51, 7034.

* cited by examiner

DEVICE AND A METHOD OF SENSING CHARACTERISTICS OF A FOOD MATERIAL AND A MACHINE AND A METHOD OF BREWING COFFEE HAVING A WAVE SOURCE WITH WAVELENGTH RANGE COMPRISING VISIBLE BAND AND NEAR INFRARED BAND

This application is the U.S. National Phase application under 35 U.S.C. §371 of International Application No. PCT/IB2014/061612, filed on May 22, 2014, which claims the benefit of International Application No. PCT/CN2013/076258 filed on May 27, 2013. These applications are hereby incorporated by reference herein.

FIELD OF THE INVENTION

This disclosure relates to food processing, and particularly relates to coffee brewing.

BACKGROUND OF THE INVENTION

In the present consumer-level food processing machines, the scheme used for processing the food has limited flexibility. Taking home/office coffee brewing machines as an example, for a selected taste, such as espresso or cappuccino, a routine is always pre-stored for brewing this selected taste. This kind of routine may consider some user inputs, such as a volume of the coffee or strength of the coffee.

OBJECT AND SUMMARY OF THE INVENTION

In the art of coffee brewing, coffee beans are roasted before grinding and brewing. Depending on the color of the roasted beans or the ground powder perceived by human eyes, the degree of roasting can also be labeled as light, medium light, medium, medium dark, dark, or very dark. Darker roasts are generally bolder because they have less fibre content and a more sugary flavor. Lighter roasts have a more complex and therefore perceived stronger flavor from aromatic oils and acids otherwise destroyed by longer roasting times. Different suppliers may roast the coffee beans to different roasting degree. Even after grinding, the coffee powder still reflects roasting degree of coffee beans and brings different coffee tastes to consumer.

In another example, the fineness of the ground coffee powder, also influences the taste. Generally, finer ground coffee powder lends itself to flavorful espresso, however if it is too fine, the resulted coffee brew may be on the bitter side. On the other hand, if the ground coffee powder is too coarse, the brew may be too weak and lacks full bodied and rich espresso flavor. Again, the fineness of ground coffee powder is not same. Different vendors may grind the beans into different fineness. In case that the user grinds the coffee beans by using a home grinder, the grinder will be worn out after using for a long time thus results in unstable fineness of ground coffee powder. Thus, the fineness of ground coffee powder used by consumer are not always same and impacts final coffee taste.

Based on the above facts, it can be seen that the brewing routines are designed according to the coffee powder with certain characteristics, e.g. a certain roasting degree and certain grinding fineness that are specific for the manufacturer. These specific characteristics may not be probably satisfied in daily use. Therefore, the brewing routines, when used in home/office, would probably make coffee with a different or deviated taste from the desired. For other application scenarios, such as soymilk making, soy bean making, the similar problems exist.

In industrial environments, measuring roasting degree is implemented by detecting the color of the coffee powder via NIR spectroscopy, which utilizes spectrometer system for detection. The wavelength range of the NIR is normally 1000 nm-2400 nm. A light source and a sensor suitable for NIR 1000 nm-2400 nm need to be used. For example, an InGaAs array capable for detecting NIR wave needs to be employed, and this InGaAs array is expensive and complicated for maintenance. Therefore, the NIR spectrometer system is difficult to be integrated into a home-use coffee machine for sensing the roasting degree.

Therefore, it is advantageous to achieve a low cost solution that can sense the characteristics of a food material such as coffee powder. It is also advantageous to have an adaptable solution of brewing coffee in the daily use of various coffee powders.

To better address one or more of these concerns, a basic idea of embodiments of the invention is using wave in both visible band and a near infrared band neighboring the visible band to detect the characteristics of food material. And another basic idea of embodiments of the invention is controlling the grinding/brewing of coffee by considering the characteristics of coffee powder.

In a first aspect of the invention, it is proposed a device of sensing characteristics of a food material, comprising: a wave source configured for emitting waves to said food material, with the wavelength range of said waves comprising a selected near infrared band neighboring a visible band; a detector, configured for detecting intensities of the waves reflected by said food material; and an analysis module, configured for determining said characteristics according to the detected intensity of the reflected waves.

In this first aspect, a near infrared band neighboring a visible band is used for detecting the characteristics of food material. A wave source and a detector in consumer level are sufficient for this band, thus this aspect is low cost and suitable for home/office use. According to experiments, detection in this band can meet the accuracy requirement in home appliance level.

In a preferred embodiment, said near infrared band comprises a wavelength range of 780 nm to 1000 nm.

In this embodiment, the near infrared band is further specified. The devices capable for the emission and detection in this band are lower cost with respect to those for 1000 nm-2400 nm band, thus the embodiment can achieve a low cost solution suitable for home/office use.

In a preferred embodiment, said wavelength range of said waves further comprises at least part of the visible band.

In this embodiment, information contained in the visible band is also detected to determine the characteristics of the food material. The accuracy is further improved.

In a preferred embodiment, said visible band comprises a wavelength range of 500 nm to 780 nm.

In this embodiment, the visible band is further specified. According to experiments, detection in these bands can meet the accuracy requirement in home appliance level.

In a preferred embodiment, said detector comprises a silicon-based sensor. In this embodiment, silicon based detectors such as a CMOS sensor, which is cheap and widely used in digital cameras and mobile phones, can be used for detecting the reflected wave. In this embodiment, the cost is low. Additionally, this embodiment also enables a feasible integration of the device into a portable device with a camera.

In a preferred embodiment, the device further comprises: a filter, configured for filtering the reflected waves and obtaining a subset of waves in predetermined subbands within said wavelength range; said detector is configured for detecting an intensity subset comprising intensities of each subband wave in said subset of waves; and said analysis module is configured for determining said characteristics according to the detected intensity subset.

In this embodiment, only waves in predetermined subbands, instead of the full band, are detected and processed to determine the characteristics of food material. First, this solution can reduce the system complexity, due to that the components for detecting subband signals are less complex in structure and processing these subbands signal is quicker than processing full band signals. Second, experiments have proven that the detection in the predetermined subbands can also guarantee the accuracy of sensing to be at an acceptable level for home appliance.

In a preferred embodiment, the device further comprises a memory storing a model for calculating the characteristic of food material according to intensity subsets; and said analysis module is further configured for inputting the detected intensity subset into the model and obtaining the characteristic of the food material outputted by the model.

In this embodiment, the characteristic of food material and the intensities of subband waves is obtained by for example the manufacturer from prior experiments. The prior experiments use food materials with various reference characteristics, and their respective intensity subsets of intensities of subband waves are used for creating a model or so-called classifier. During daily use, the practically detected intensities of subband waves are inputted into the model, and the model will calculate a characteristic of the detected food material. The sensing accuracy is high and sufficient for home use.

In a preferred embodiment, said filter comprises any one of: a filter wheel with a plurality of filtering lenses, said lenses corresponding to each of the subbands, the wheel configured for being rotated to obtain each subband wave; and a grating configured for separating each subband wave from the reflected waves.

This embodiment proposes two implementations of the filter. The filter wheel solution can be used together with a time dividing detection, wherein the filter wheel is rotated for outputting one subband wave at one time. And the grating solution can be used together with a spatial dividing detection, wherein a plurality of sensors are deployed in different locations, with each of them for receiving one subband wave refracted by the grating.

In a preferred embodiment, the food material comprises coffee powder, and the characteristics comprise at least any one of: roasting degree of coffee powder; and grind fineness of coffee powder.

This embodiment proposes the application of the invention in coffee brewing, and is especially advantageous for home/office-use coffee machines.

In a second aspect of the invention, it is proposed a machine of brewing coffee, comprising: a first device, configured for determining parameters for brewing coffee according to the roasting degree of coffee powder; and/or a second device, configured for determining parameters for brewing coffee according to grind fineness of coffee powder.

In this aspect, the coffee machines can determine the brewing parameters further according to the characteristics of the coffee powder, such as the roasting degree (also reflected as color) and the grind fineness, thus provides an adjustable coffee brewing solution.

These and other aspects of the invention will be apparent from and elucidated with reference to the embodiment(s) described hereinafter.

BRIEF DESCRIPTION OF THE DRAWINGS

Features, aspects and advantages of the present invention will become obvious by reading the following description of non-limiting embodiments with the aid of appended drawings.

DETAILED DESCRIPTION

Figure 1:
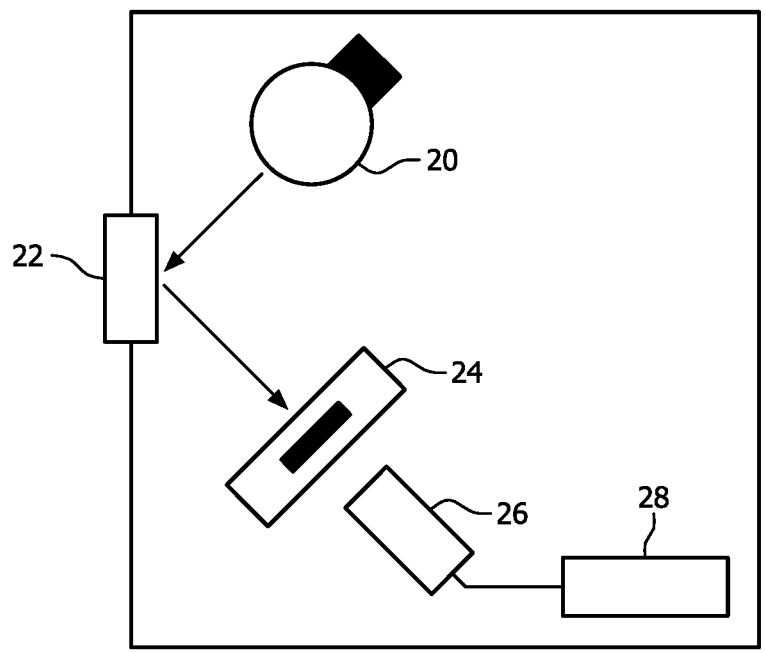
FIG. 1 shows a schematic structure of the device according to an embodiment of the invention.

As schematically shown in FIG. 1, according a first aspect of the invention, it is provided a device of sensing characteristics of a food material. The device comprises: a wave source 20 configured for emitting waves to said food material, with the wavelength range of said waves comprising a selected near infrared band neighboring a visible band; a detector 26, configured for detecting intensities of the waves reflected by said food material; and an analysis module 28, configured for determining said characteristics according to the detected intensity of the reflected waves.

Although there are minor differences in exact wavelength values, the visible band is generally considered as from about 340 nm to about 780 nm. In this case, the near infrared band comprises a wavelength range of 780 nm to 1000 nm. Compared with the current NIR sensing solution with a wavelength range higher than 1000 nm, the advantage of the embodiment is that this device can use a low cost detector suitable for the wavelength range of 780 nm to 1000 nm without using expensive detector for NIR higher than 1000 nm.

In a preferred embodiment, the wavelength range of said waves also comprises at least a part of the visible band. And more specifically, the part of the visible band comprises a wavelength range of 500 nm to 780 nm. Compared with the current NIR sensing solution which collects waves with a wavelength from 1000 nm to 2400 nm, this embodiment has the following advantages: 1. the VIS (visible band) light source is low cost, such as a common incandescent lamp or fluorescent lamp; and 2 making an industrialization use of the roasting information embedded in the color (visible band) of the ground coffee powder, while the current NIR sensing does not collect waves in the visible band. In a more complex embodiment, the wavelength range of said waves also comprises the full range of the visible band, namely from about 340 nm to about 780 nm.

In a preferred embodiment, since the detection is on the visible band and the selected near infrared band neighboring the visible band, a silicon-based sensor, such as a CMOS sensor is sufficient for detecting the intensities of the waves in these bands. The silicon-based sensor is lower cost than common NIR sensor such as InGaAs array suitable for a wavelength of 1000-2400 nm.

In practice, the above embodiments can be embodied in various implementations. In one implementation, the device is a standalone device. In another implementation, the device can be integrated in to a mobile phone, wherein the wave source 20 can be the flash light of the phone, the detector 26 can be the camera of the phone, and the analysis module 28 is implemented by a dedicated circuit in the phone or by a software module executed by the processor of the phone. These two types can be portable. In still another implementation, the device can be installed in a food processing machine, such as a coffee machine. The device senses characteristics of food material, and the scheme of food processing is determined by the sensed characteristics of food material. In this case, the device also has a sample window 22 made in transparent glass or plastic which allows the emitted waves and/or the reflected waves to pass through. This implementation will be elucidated in more details in the following part.

The above part describes the basic components of the device, and the principle of sensing the characteristics will be described below. Coffee powder is taken as an example to elucidate the principle, but it should be noted that other food materials, such as soybeans, are also applicable.

It is known that the powder color of coffee beans with different roasting degree is different. The color of coffee powder has relationship with the roasting degree of coffee beans. The color can be represented by the intensities of the waves, reflected by the coffee powder, with a plurality of visible range wavelengths. Similarly, the difference of roasting degrees also results in difference of intensity at NIR wavelengths. It should be noted the term "color" covers the intensities of waves in both the visible band and the selected near infrared band neighboring the visible band.

The spectra in the visible band and NIR band neighboring the visible band, namely the intensities of the waves at these wavelengths, can be used to create a model or so-called classifier. The spectra for each of various roasting degrees are obtained by the manufacturer via experiments. To have a consistence between the experiments and daily use, the experiment should preferably in the same environmental condition as daily use, such as in the same illumination level. The spectra and its corresponding roasting degree are used to create the model. The model is stored in the memory of the device. And the analysis module determines the characteristic, such as the roasting degree of the sample coffee powder by using the measured spectra as an input of the model and obtaining the output roasting degree of the model. The detailed method of creating the model can be a deemed as the training process. Those skilled in the art could adapt the common training process in the art to meet the specific purpose of the application. The present disclosure would not give unnecessary details. It is should be noted that the sensor can be used for sensing a plurality of characteristics. For example, the sensor can be used for sensing either the roasting degree or the ground fineness. In this case, for each characteristic, the model would be different. Therefore, there may be a plurality of models stored in the memory.

Preferably, instead of analyzing a full band of visible band (VIS) and the near infrared band (NIR) neighboring the VIS, only predetermined subbands are detected and analyzed, so as to save cost of the detector, as well as to levitate the processing burden for the analysis module. To this end, in a preferred embodiment, as shown in FIG. 1, the device further comprises a filter 24, configured for filtering the reflected waves and obtaining a subset of waves in predetermined subbands. The predetermined subbands are within the wavelength range of 500 nm-1000 nm. The numbers and range of these subbands can be flexibly adjusted according to the accuracy requirement. The higher the accuracy requirement is, the more subbands are needed to differentiate the colors. In an example, a wavelength range in which the spectra of different colors differ significantly from each other can have more subbands therein, while a wavelength range in which the spectra of different colors are almost the same can have less or no subbands therein for detection. In one preferred embodiment, the subbands are 500-550 nm, 550-600 nm, 600-650 nm, 750-800 nm, 850-900 nm. It could be understood that these subbands are only examples, and other numbers and locations of the subbands are also applicable thus are also within the scope of the invention. These subbands can be either continuous or discrete.

There are many embodiments of the filter. In one embodiment, the filter 24 is a filter wheel with a plurality of filtering lenses. Each lens corresponds to one of the subbands. The wheel is configured for being rotated to provide each subband wave in a time-dividing manner In one case, the lenses are band pass filters with a pass band of that subband, such as a piece of colored glass. For example, to obtain a subband of 500-550 nm, a band pass filter with a pass band of 500-550 nm can be used. In another case, the lenses are high pass or band pass filers with a pass-band difference the same as desired subband. Their transmission curves can be shown in FIG. 2 by way of example, and the differences of pass-band between each two neighboring filters are just the above subbands. The analysis module would obtain an intensity of a subband A by subtracting an intensity of wave passed by the higher subband filter from the intensity of the wave passed by the lower subband filter. For example, to obtain a subband of 500-550 nm, a subtraction can be done between the output of two high-pass filters, 500 nm-(1000 nm) and 550 nm-(1000 nm) respectively.

In another embodiment, the filer comprises a grating configured for separating each subband wave from the reflected waves in a spatial dividing manner The detector may comprise a plurality of CMOS sensors, each of which is arranged at a location to receive one separated subband.

In the above embodiment, the color of coffee powder (corresponding to roasting degree of coffee beans) is sensed. In another embodiment, the grind fineness of the coffee powder is sensed.

However, the subbands for fineness detection may be different from those for color (roasting degree) detection. Those skilled in the art would envisage how to implement a device for sensing the grind fineness on the basis of the above teaching about color (roasting degree).

After elucidating a first aspect of sensing the color (roasting degree)/grind fineness of coffee powder, the following part will elucidate a second aspect of optimizing coffee brewing according to the color (roasting degree)/grind fineness of coffee powder.

In coffee brewing procedure, water penetrates to the pores of the coffee granules and displaces air between the particles. Soluble elements (from coffee, either preexisting or resulting from hydrolysis) dissolve into water in the pores of the coffee granules. These elements diffuse through the water in the pores to the spherical surface of the granules. There is mass transfer by convection from the surface to the bulk of the water surrounding the granules. When making espresso coffee, hot pressurized and vaporized water is forced through ground coffee powder. Brewing parameters such as water temperature, brewing time, pressure influence the taste of the coffee. Experiments also prove that roasting degree/grind fineness of coffee powder influence the taste of the coffee.

Figure 3:
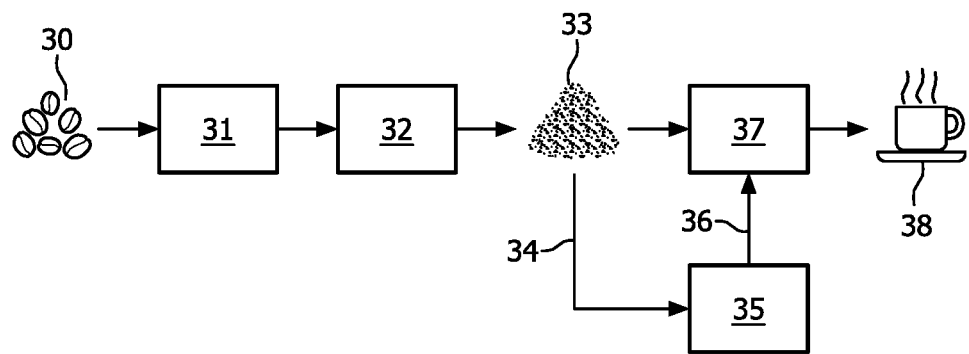
FIG. 3 shows a flow chart of brewing coffee according to another embodiment of the invention.

An embodiment of the invention comprises the step of determining the brewing parameters according to the color/grind fineness of coffee powder, so as to provide a desired taste. A procedure of brewing coffee according to this embodiment is shown in FIG. 3.

Firstly, the coffee beans 30 are roasted in step 31, and the roasted coffee beans are ground in step 32. Coffee powder 33 is obtained. After that, wave intensities 34 are obtained in step 35. In step 35, the color and/or the grind fineness of the coffee powder is sensed and the brewing parameters 36 for the brewing procedure 37 is adjusted. After brewing, coffee 38 is made.

In step 35, according to the color (roasting degree) of coffee powder, brewing parameters, e.g. water temperature, pressure and brewing time, can be adjusted to extract the flavor of coffee. Relevant parameters can also be determined by the obtained grind fineness. For example, if the grinds are too fine, the brewing time will be set shorter, or/and temperature will be set lower, or/and pressure will be set lower. On the other hand, if the grinds are too coarse, the brewing procedure can also be adjusted accordingly.

To this end, the machine of brewing coffee according to the invention comprises: a first device, configured for determining parameters for brewing coffee according to color of coffee powder; and/or a second device, configured for determining parameters for brewing coffee according to grind fineness of coffee powder.

The coffee machine can obtain the color and/or grind fineness of coffee powder through user input. Alternatively, the coffee machine can also automatically detect these characteristics. One solution is ultrasonic detection; and another solution is to integrate the device according to the above first aspect of the invention. The disclosure will elucidate this integration.

Figure 4:
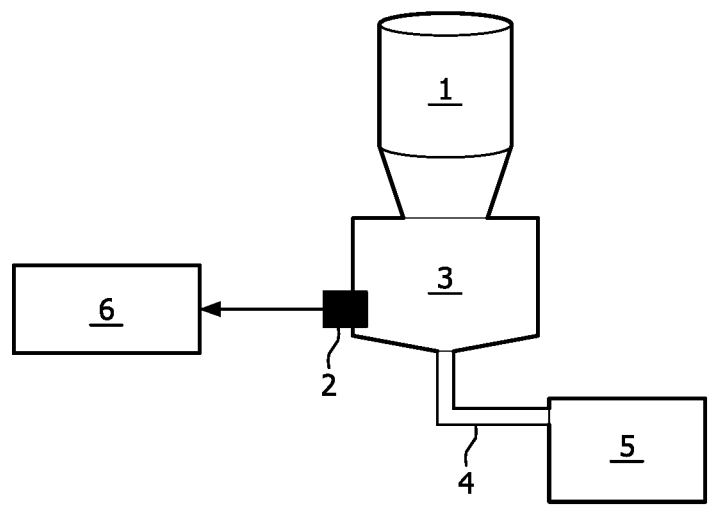
FIG. 4 shows schematic structure of a coffee machine with the device according to an embodiment of the invention.

FIG. 4 schematically shows a structure of a coffee machine. The machine includes a coffee bean holder 1, a device 2 of sensing fineness/color (roasting degree) of coffee powder according to an embodiment of the invention, a grinder unit 3, a coffee powder discharge chute 4, a filter unit 5 and a controller 6. The controller 6 comprises the above first device and the second device for controlling brewing parameters.

The device 2 senses the fineness and/or the color of coffee powder, and sends the information to the controller 6. The controller 6 is a MCU or the like. It processes the information and determines the parameters in brewing procedure according to the fineness and/or the color of coffee powder. The parameters can be determined with other information, e.g. user input information. The coffee machine may have a storage device, such as ROM or flash memory to store mapping tables which set forth the correlation between different fineness level and/or the colors of coffee powder and their corresponding brewing parameters. The controller 6 may search the stored table and select a brewing parameter corresponding to the detected fineness and/or the color. It should be noted that the brewing parameters are not limited to water temperature, time for brewing and pressure. All conditions in the brewing procedure that can be adjusted to make a contribution to the taste of the coffee fall into the scope of brewing parameters.

For a coffee machine without grinder, the device 2 may be installed in the coffee powder holder. For Espresso machine which comprises a grinder, the device 2 can also be installed beside the passage of coffee powder between the grinder and brewing unit, but the installation place is not limited to the mentioned. For instance, in one embodiment, as illustrated in FIG. 4, the device 2 may be installed on the wall of grinder, the coffee powder discharge chute 4, or the filter unit 5.

Additionally, for a coffee machine with a grinder, the quality of grinder can also be indicated by the fineness of the coffee powder ground by the grinder. The controller 6 analyzed the sensed fineness of coffee powder, when the fineness is out of a predetermined scope, a warning message will be sent to users to ask them check or replace the grinder components, e.g., the blades.

The above part elucidates the device and method of the invention to sense the characteristics of coffee powder. The following part would give experimental results from proof-of-principal experiments to show the feasibility and accuracy of embodiments of the invention.

Roasting Degree (Color)

In a proof-of-principal experiment, coffee roasted at three degrees is tested. Coffee beans from 8 places of origin are roasted with a Probat Emmerich roaster, taken out at the start of the first crack, at the start of the second crack and 1~2 minutes after the second crack, regarded as test samples at a roasting degree of light, medium and dark, respectively. The roasted beans are then ground at various grinding finenesses by a standalone grinder (Rocky DOSER). The grounds are scanned at a test VIS-NIR optical platform. The intensities of reflected waves are analyzed, based on which the color (roasting degree) is classified by a classification algorithm.

Figure 2:
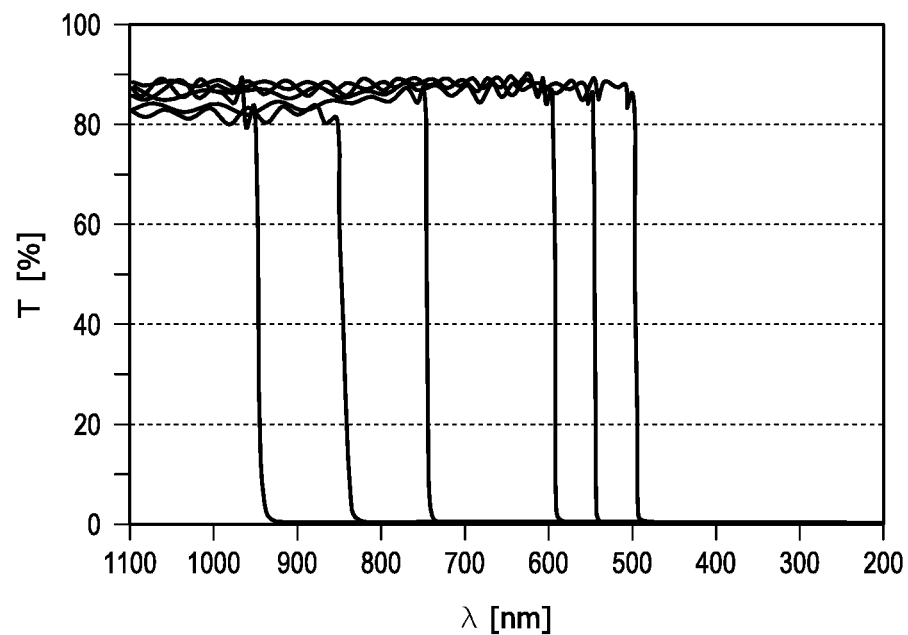
FIG. 2 shows the cut-off wavelengths of the high pass filters for an embodiment of the invention.

In this experiment, a simplified optical sensing configuration is applied, using six high pass filters with cut-off at 500 nm, 550 nm, 600 nm, 750 nm, 850 nm and 950 nm (FIG. 2).

The classification performance is listed in Table 1.

TABLE 1

| | Roasting degree | | |
|---|---|---|---|
| | Light | Medium | Dark |
| Accuracy | 99.3% | 86.5% | 87.8% |

It can be seen that all three roasting degrees are detected with an accuracy of >85%, with 'Light' at >99%. This accuracy can meet the requirement in home/office use.

Fineness

Eight kinds of green Arabia coffee beans from different origins including Peru, Colombia, Salvador, Guatemala, Kenya, Tanzania Kilimanjaro, India, Tanzania were purchased from market. The green beans were handpicked to discard bad beans.

Coffee bean was roasted in the lab using a pilot roaster (Probat, Emmerich am Rhein, Germany) at constant power input. Each coffee was roasted to three levels (light, medium, and dark). The roasting procedure is as follows:

About 50 g of green coffee beans was roasted each time. The roaster is pre-warmed to 185° before the green bean is poured into the drum. The drum temperature drops when the bean is added. The first crack of coffee bean normally occurs (the temperature was about 175) roughly at 7 minutes into roasting. Sample collected at this stage is regarded as light roast. Continue roasting to the beginning of the second crack, which occurs around 9 min and 185°, produces medium roasted coffee. When the second crack is finished, the heat is turn off and bean is roasted for another one minute. Sample collected at this final stage is regarded as dark roast. All roasted coffee beans were cooled and saved in a sealed container with desiccant. Before the next roasting, the temperature of roaster needs to drop below 150°.

In order to obtain a representative set of coffee samples, all roasting conditions sets were applied for three times each, producing a total number of 72 coffee samples (8 origins×3 roasting degrees×3 roasting process replicates).

Roasted coffee beans were grinded into three levels (fine, medium, and coarse) using a household coffee grinder (Rocky DOSER, Rancilio, ITALY) with the fineness adjuster set at 0, 20, and 50, respectively. With three levels of grinds fineness, a total of 216 ground coffee samples were obtained (72 kinds×3 particle sizes). All roasted coffee beans were ground and labeled and saved in a sealed container with desiccant.

The samples were placed in a 10 mm×10 mm glass cuvette, and scanned at a lab sensing setup where 6 band-pass optical filters were used with a wavelength range between 500 nm and 1050 nm. Three replicates were collected for each individual sample at different positions of the cuvette.

Figure 5:
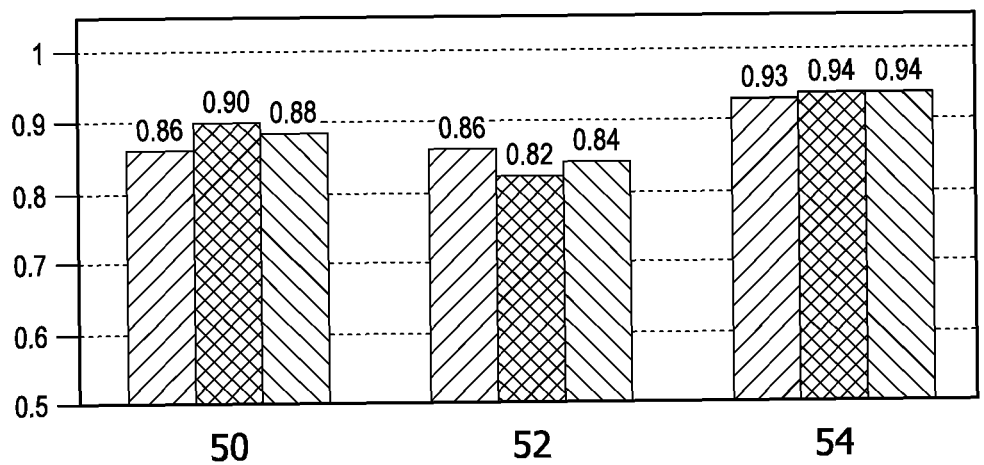
FIG. 5 shows the accuracy of sensing grind fineness according to an embodiment of the invention.

Data were collected in data acquisition unit and processed in Matlab where grinding fineness was classified by a multinomial logistic regression algorithm. The result is shown in FIG. 5. Fineness 50 denotes fine, 52 denotes medium, and 54 denotes coarse. For each fineness, the first bar represents the sensitivity, the second bar represents PPV, and the third bar represents the accuracy for classification of coffee grinds fineness. It can be seen that the averaged accuracy is over 88%.

Those ordinary skilled in the art could understand and realize modifications to the disclosed embodiments, through studying the description, drawings and appended claims. For example, in the above embodiment, the device 2 of sensing characteristics of coffee powder is integrated into the coffee machine. In an alternative embodiment, the device 2 can be a standalone device, or realized in a mobile phone by reusing its flash light, camera, and processor.

The term "food material" covers any material that is to be processed for making eatable or drinkable item. The food material can be directly eaten or drunk. Or, it can not be eaten directly but can be processed or brewed to make food or beverage, such as coffee powder or tea leaf. The word "comprising" does not exclude the presence of elements or steps not listed in a claim or in the description. The word "a" or "an" preceding an element does not exclude the presence of a plurality of such elements. In the practice of present invention, several technical features in the claim can be embodied by one component. In the claims, any reference signs placed between parentheses shall not be construed as limiting the claim.

What is claimed is:

1. A device of sensing at least any one of roasting degree of coffee powder and grind fineness of coffee powder, comprising:
   a wave source configured for emitting waves to said coffee powder, the wavelength range of said waves comprising at least part of visible band and a selected near infrared band neighboring the visible band;
   a detector, configured for detecting intensities of the waves reflected from said coffee powder; and
   an analysis module, configured for determining said roasting degree of coffee powder and/or said grind fineness of coffee powder according to the detected intensities of the reflected waves.

2. The method of claim 1, wherein said near infrared band is in a wavelength range of 780 nm to 1000 nm.

3. The device of claim 1, wherein said at least part of the visible band is in a wavelength range of 500 nm to 780 nm.

4. The device of claim 1, wherein said detector comprises a silicon-based sensor.

5. The device of claim 1, further comprising:
   a filter, configured for filtering the waves reflected from said coffee powder and obtaining a subset of waves in predetermined subbands, said predetermined subbands being in said wavelength range;
   said detector is configured for detecting an intensity subset comprising intensities of each subband wave in said subset of waves;
   and said analysis module is configured for determining said roasting degree of coffee powder and/or said grind fineness of coffee powder according to the detected intensity subset.

6. The device of claim 1, further comprising:
   a memory storing a model for calculating said roasting degree of coffee powder and/or said grind fineness of coffee powder according to intensity subsets;
   and said analysis module is further configured for inputting the detected intensity subset into the model and obtaining said roasting degree of coffee powder and/or said grind fineness of coffee powder outputted by the model.

7. The device of claim 5, wherein said filter comprises any one of:
   a filter wheel with a plurality of filtering lenses, said lenses corresponding to each of the subbands, said filter wheel configured for being rotated to obtain subband waves; and
   a grating configured for separating each subband wave from the reflected waves.

8. A method of sensing at least any one of roasting degree of coffee powder and grind fineness of coffee powder, comprising steps of:
   emitting waves to said coffee powder, the wavelength range of said waves comprising at least part of visible band and a selected near infrared band neighboring the visible band;
   detecting intensities of the waves reflected by said coffee powder; and
   determining said roasting degree of coffee powder and/or said grind fineness of coffee powder according to the detected intensities of the reflected waves.

9. The method of claim 8, wherein said at least part of the visible band is in a wavelength range of 500 nm to 780 nm.

10. The method of claim 8, further comprising a step of:
    filtering the reflected waves reflected from said coffee powder and obtaining a subset of waves in predetermined subbands, said predetermined subbands being in said wavelength range;
    said step of detecting further comprising:
    detecting an intensity subset comprising intensities of each subband wave in said subset of waves;
    said step of determining further comprising:
    determining said roasting degree of coffee powder and/or said grind fineness of coffee powder according to the detected intensity subset.

11. The method of claim 8, wherein said determining step further comprising:
    determining said roasting degree of coffee powder and/or said grind fineness of coffee powder by matching said detected intensity subset into a correlation, said correlation being predetermined and reflecting the relationship between said roasting degree of coffee powder and/or said grind fineness of coffee powder and its respective intensity subsets.

12. The method of claim 8, wherein said near infrared band is in a wavelength range of 780 nm to 1000 nm.

* * * * *